United States Patent [19]
Amiral et al.

[11] Patent Number: 5,175,112
[45] Date of Patent: Dec. 29, 1992

[54] SUBMICRON PARTICLES, PREPARATION AND UTILIZATION IN IMMUNODIAGNOSIS

[75] Inventors: Jean Amiral, Franconville; Pascale Laroche, Nancy, both of France

[73] Assignee: Diagnostica Stago, Asnieres, France

[21] Appl. No.: 576,466

[22] PCT Filed: Jan. 22, 1990

[86] PCT No.: PCT/FR90/00045
§ 371 Date: Sep. 12, 1990
§ 102(e) Date: Sep. 12, 1990

[87] PCT Pub. No.: WO90/08321
PCT Pub. Date: Jul. 26, 1990

[30] Foreign Application Priority Data

Jan. 20, 1989 [FR] France ................... 89 00660
Apr. 12, 1989 [FR] France ................... 89 04819

[51] Int. Cl.$^5$ ............... G01N 33/546; G01N 33/547; G01N 33/531
[52] U.S. Cl. .................. 436/533; 436/534
[58] Field of Search ................ 436/533, 534

[56] References Cited
U.S. PATENT DOCUMENTS 4,571,382  2/1986  Adachi ............... 435/7.23
4,600,698  7/1986  Toth ................. 436/533
4,829,101  5/1989  Kraemer et al. ...... 525/286

FOREIGN PATENT DOCUMENTS 1384399  2/1975  United Kingdom .

Primary Examiner—Mary E. Ceperley
Attorney, Agent, or Firm—Foley & Lardner

[57] ABSTRACT

The present invention relates to a method of binding an immunological material, selected from antigens and antibodies, to submicron latex particles by covalency or adsorption, in which method, which comprises the stabilization of the latex, (A) (1) acrylic latex particles based on polybutyl methacrylate, whose mean diameter is less than or equal to 100 nm, said latex containing a molar quantity of butyl methacrylate units greater than 50%, having a density of 0.9 to 1.4 g/cm$^3$ and containing from 100 to 450 microequivalents of COOH groups per gram of latex, are brought into contact, in an appropriate liquid medium having an ionic strength in the range from 0.01 to 0.5 at a pH of 4 to 10, at a temperature of 0° to 60° C., with (2) the immunological material to give latex particles sensitized by an immunological material and such that said immunological material is bound to each latex particle, and (B) said immunological reagent obtained in this way is stabilized by means of a stabilizing material selected from the group consisting of hydroxylated substances containing one or, preferably, several OH groups per molecule, protein-type substances, peptide-type substances, amino acids, polyose-type substances containing one or more carboxylic acid and/or carboxylate groups, polyvinylpyrrolidone and mixtures thereof.

It further relates to the immunological reagent obtained by this method and to its use in the field of immunoassays.

18 Claims, 10 Drawing Sheets

SUBMICRON PARTICLES, PREPARATION AND UTILIZATION IN IMMUNODIAGNOSIS

FIELD OF THE INVENTION

The present invention relates, by way of novel industrial products, to submicron latex particles (i.e. latex particles with a mean diameter of less than 1 micrometer) sensitized by an immunological material, that is to say particles to which an antigen or antibody is bound by covalency or adsorption. These particles are "invisible" or "transparent" when they are exposed to electromagnetic radiation such as visible light and UV, and become "visible" due to agglutination when they are exposed to said radiation after having been brought into contact with an antibody or antigen, respectively.

The present invention further relates to the method of preparing these sensitized particles and to their use in immunoassays involving reactions of the antigen/antibody type.

PRIOR ART

Immunological techniques occupy an important position in the area of biomedical analysis. They are now employed for quantifying or assaying numerous substances, among which proteins, haptens, hormones, drugs and antibodies may be mentioned in particular.

Their principle is based on the chemical binding of an antibody (or antigen) to a particulate support. The complex of particulate support and antibody or antigen constitutes a reagent; this reagent agglutinates rapidly when brought into contact with the corresponding antigen (or antibody). This agglutination is accompanied by a substantial increase in the absorbance of the medium as a function of the particle size. The particle therefore behaves as a passive agglutination-amplifying factor, resulting in a sharp increase in the absorbance.

Of the known techniques, three groups of methods have gained recognition in immunoanalysis.

The first group comprises the methods of turbidimetry and nephelometry. These are methods which are rapid to carry out but have a low sensitivity and can be used only for high protein concentrations, especially in the case of turbidimetry, which entails protein concentrations above 100 µg/ml. Nephelometry is more sensitive (with use concentrations of the order of 20 µg/ml) but requires very "specialized" equipment and prior treatment of the samples, which greatly restrict the possible uses.

The second group comprises the so-called LAURELL and MANCINI methods. These are simple methods but are slow to carry out and cannot be automated. They apply to protein concentrations above 20 µg/ml in the case of the MANCINI method and above 5 µg/ml in the case of the LAURELL method. The analysis times are several hours and often more than 24 hours.

The third group comprises the so-called labeling methods, especially the enzyme immunological methods (EIA) and radioimmunological methods (RIA). The apparatus required to carry them out is expensive, the assays consist of several reaction steps separated by washes, they are still complicated to automate and the analysis times cannot easily be reduced to less than two hours. On the other hand, these methods permit sensitivities of less than 1 ng/ml and apply to any biological substance present at concentrations advantageously in the range from 10 ng/ml to 1 mg/ml.

This situation justifies and explains the research efforts currently being made to develop novel immunoassay methods which overcome the afore-mentioned disadvantages with a view to improving the use conditions of the techniques of the first two groups when the high sensitivity of the EIA and RIA methods is not absolutely necessary.

It is known in particular that, since 1970, authors have been applying themselves to the task of refining the method of detecting immunological reactions of the antigen/antibody type belonging to the first two groups mentioned above. Thus the use of latex microparticles coated with an antigen or antibody has been envisaged for perfecting quantitative assays by turbidimetry, nephelometry and particle counting.

In the field of turbidimetry (by measurement of the light absorbance), the use of submicron latex particles (mean diameter: 0.79 micrometer) coated with anti$\beta_2$-microglobulin antibodies for assaying $\beta_2$-microglobulin by measurement of the absorbance at 360 nm is known from the articles by A. M. BERNARD, A. VYSKOCLL and R. R. LAUWERYS, Clin. Chem., 27 (n° 6), pages 832–837 (1981) and by A. M. BERNARD and R. R. LAUWERYS, Clin. Chim. Acta, 119, pages 335–339 (1982); the use of monoclonal or polyclonal anti-IgG antibodies for assaying serum immunoglobulins in microcups is known from the article by Y. MAYNARD et al., Clin. Chem., 32 (n° 5), pages 752–757 (1986).

In the field of nephelometry (by measurement of the light diffusion), the use of submicron latex beads (mean diameter: 0.3 micrometer) coated with an anti-rabbit IgG antibody for assaying rabbit IgG is known from the article by J. GRANGE et al., Journal of Immunological Methods, 18, pages 365–375 (1977). The latex beads consist of carboxylated polystyrene containing COOH groups for binding the ligand, which in this case is the anti-rabbit IgG antibody. Said article points out especially that "the preparation of latex spheres containing adsorbed antigens or antibodies is difficult to standardize because of their tendency to undergo autoagglutination when the pH and the ionic strength of the assay medium change".

Also, the use of latex spheres (polystyrene) with a diameter of 300 nm, covalently bound to an antibody, for performing nephelometric assays (reading at a wavelength of 550 nm and at an angle of observation of 90°) is known from the article by Anne-Marie BONNEFOY et al., C. R. Acad. Sc. Paris, 283, series D, pages 115–118 (Jul. 5, 1976). Said article neither describes nor suggests the method of stabilizing the immunological reagent which consists of said latex spheres covalently bound to the antibody and stabilized.

In the field of particle counting, the use of submicron polystyrene particles (mean diameter: 0.8 micrometer) coated with human IgG for assessing the agglutination in the presence of an agglutinating agent such as rheumatoid factor is known from the article by C. L. CAMBIASO and P. L. MASSON "Automated determination of circulating immune complexes by particle counting immunoassay (PACIA)", Protides and Biological Fluids, 1–4 (1979), are also known the two afore-mentioned articles by A. M. BERNARD et al. and the paper entitled "Une nouvelle génération de dosages immunologiques, non-isotopiques par comptage de particules de latex" ("A new generation of non-isotopic immunoassays by counting latex particles") given by J. C. MARESCHAL at the 30th journées nationales de l'APDILA, held in Paris on Nov. 16 and 17, 1985, which emphasizes the difficulties encountered when carrying out measurements involving the agglutination of latices, such as the difficulty of quantifying the agglutination reaction, the high frequency of non-specific agglutination and the lack of sensitivity.

In summary, the turbidimetric, nephelometric and particle counting methods are limited by several disadvantages, namely:

difficulties of preparing stable and standardized suspensions, spontaneous autoagglutination of latices sensitized by an antibody or antigen, small measuring range of the calibration curve (variation in optical density (OD) not exceeding 0.3 to 0.4), lack of sensitivity and reproducibility, treatment of the particulate reagent before use, in certain cases (for disaggregation), and poor stability of the reagent, and difficulty of carrying out the methods and sometimes complicated detection.

These disadvantages are such that these methods have not been exploited, despite their practical interest.

Furthermore, the use of submicron spherical particles of polystyrene latex (mean diameter: 0.057 micrometer) on to which an antibody has been adsorbed, in this case an anti-C-reactive protein antibody, for assessing, by (preferably) particle counting, turbidimetry or nephelometry, the agglutination resulting from bringing the complex of latex spheres and anti-C-reactive protein into contact with C-reactive protein (abbreviated to CRP) is known from the article by J. WINKLES et al. "Enhanced-Latex-Agglutination Assay for C-Reactive Protein in Serum, with Use of a Centrifugal Analyzer", Clin. Chem., 33 (n° 5), pages 685-689 (1987). The technique described by J. WINKLES et al. involves sonication, which is considered to be essential for dispersing and stabilizing the latex particles (in order to prevent their autoagglutination) and hence for enabling these particles to be used for adsorbing the immunological material (the anti-CRP antibody in the case in question in said article). Sonication, which has to be repeated each time before using the immunological reagent consisting of the immunological material adsorbed on said latex particles, demands the use of expensive equipment (namely the ultrasonic generator and its enclosure) and the use of complicated operating conditions, upsetting or limiting the possibilities of reproducing said technique. Reference is made in this connection to the information given in said article, page 686, left-hand column, lines 37-58, and page 688, right-hand column, lines 54-62.

In summary, the technique of J. WINKLES et al., for immunoassays of the antigen/antibody type, demands the use of an ultrasonic field for a period of 60 s; if this period exceeds 60 s, it causes overheating and destroys the complex of latex spheres and antibody, and if sonication is incomplete, the sensitivity of the assay with the resulting complex of latex spheres and antibody decreases considerably, ultimately falsifying the results of the assay.

It is also known that the latex used to bind antigens or antibodies in the form of spheres, membranes or walls must be stabilized in particular by means of a polyhydroxylated or protein-type substance or else polyvinylpyrrolidone (see especially EP-A-0 104 101, FR-B-2 125 000, FR-A-2 495 326, EP-A-0 140 489, EP-A-0 280 560, EP-A-0 163 393 and EP-A-0 281 327).

It so happens that the choice of latex is of particular importance. In fact, it has been found that submicron latex particles, especially those according to EP-A-0 296 883 (carboxypolypropylene latex), EP-A-0 286 687 (ethylene/acrylic acid and ethylene/methacrylic acid copolymer latices), EP-A-0 295 402 (styrene/acrylic acid/triethylene glycol methacrylate copolymer latex), FR-B-2 125 000 (polystyrene or polyacrylamide latex and butadiene/styrene, acrylonitrile/butadiene/styrene or vinyl acetate/vinyl acrylate copolymer latex) and FR-A-2 495 326, EP-A-0 140 489 and EP-A-0 280 560 (polystyrene, polyacrylamide, polyethylene or polypropylene latex), even when associated with a stabilizing material, are not stable with time. These particles sensitized by an immunological material such as an antigen or antibody are subject to autoagglutination phenomena after storage for 2-4 months under the conventional conditions.

To improve the stability during storage at 4° C., it would be better to use a dilute immunological reagent.

AIM OF THE INVENTION

There is a need for an immunoassay technique, using antigens or antibodies bound to submicron latex particles by covalency or adsorption, which is relatively simple, differs from the EIA and RIA techniques, makes it possible to overcome the afore-mentioned disadvantages of the prior art, ensures a rapid determination which can easily be automated and is accessible to any analytical or research laboratory, has a vast field of application and makes it possible to achieve a sensitivity threshold of at least 100 ng/ml.

There is also a need for a technique for preparing submicron latex particles, sensitized by an immunological substance or material, which are stable with time during storage without having to be diluted in an appropriate biological buffer.

According to the invention, it is proposed to meet the above-mentioned needs by providing a novel technical solution which on the one hand uses submicron particles of a particular latex and on the other hand overcomes the afore-mentioned disadvantages of the prior art.

SUBJECT OF THE INVENTION

According to the invention, a novel technical solution is recommended for the preparation of latex particles sensitized by an immunological material with a view to performing immunoassays of the antigen/antibody type by the agglutination of latex particles coated with an antigen (or antibody) by adsorption, when said particles are brought into contact with the corresponding antibody (or antigen).

This novel technical solution comprises on the one hand choosing a particular latex and on the other hand blocking or occupying those active sites of the particles which are not occupied by the immunological material (antigen or antibody) with a stabilizing material selected from the group consisting of hydroxylated substances containing one or, preferably, several OH groups per molecule, protein-type substances, peptide-type substances, amino acids, polyose-type substances containing one or more carboxylic acid and/or carboxylate groups, polyvinylpyrrolidone, analogs thereof and mixtures thereof.

According to a first feature of the invention, a method of binding an immunological material, selected from antigens and antibodies, to submicron latex particles by covalency or adsorption is recommended, in which method, which comprises the stabilization of the latex, (A) (1) acrylic latex particles based on polybutyl methacrylate, whose mean diameter is less than or equal to 100 nm, said latex containing a molar quantity of butyl methacrylate units greater than 50%, having a density of 0.9 to 1.4 g/cm$^3$ and containing from 100 to 450 microequivalents of COOH groups per gram of latex, are brought into contact, in an appropriate liquid medium having an ionic strength in the range from 0.01 to 0.5 at a pH of 4 to 10, at a temperature of 0° to 60° C., with (2) the immunological material to give latex particles sensitized by an immunological material and such that said immunological material is bound to each latex particle, and (B) said immunological reagent obtained in this way is stabilized by means of a stabilizing material selected from the group consisting of hydroxylated substances containing one or, preferably, several OH groups per molecule, protein-type substances, peptide-type substances, amino acids, polyose-type substances containing one or more carboxylic acid and/or carboxylate groups, polyvinylpyrrolidone and mixtures thereof.

According to a second feature of the invention, the immunological reagent which consists of said particles coated with said adsorbed immunological material and said stabilizing material, and which is obtained by the method referred to above, is recommended as a novel industrial product, the dimensions of said immunological reagent being such that, during analysis under radiation of a given wavelength ($\lambda$), the ratio wavelength ($\lambda$)/mean diameter (d) of said particles is greater than or equal to 5/1.

More particularly according to the invention, said latex particles will be such that (i) said particles coated with said immunological substance and said stabilizing material and suspended in an aqueous liquid medium are invisible when exposed to radiation with a wavelength ($\lambda$) greater than the mean diameter (d) of said particles, and (ii) said particles coated with said immunological substance and said stabilizing material and suspended in said aqueous liquid medium become "visible" due to agglutination when exposed to said radiation after having been brought into contact with a substance selected from antibodies and antigens, respectively, and corresponding to said immunological substance bound to said particles.

According to a third feature of the invention, the use of this immunological reagent is recommended in the field of immunoassays of the antigen/antibody type.

The assay methods according to the invention comprise direct determination of an antibody by agglutination after said antibody has been brought into contact with a reagent consisting of latex particles each bound to an antigen by covalency or adsorption and stabilized;

direct determination of an antigen by agglutination after said antigen has been brought into contact with a reagent consisting of latex particles each bound to an antibody by covalency or adsorption; and inhibition of the agglutination of the latex/antigen reagent in the presence of the corresponding antibody and indirect assay of the free antigen (especially by competition), or vice-versa.

These assay methods are insensitive to temperture under the conventional use conditions and can be carried out at a temperature of 0° to 60° C., in particular 4° to 60° C., and especially at a temperature conventionally used in the field of immunology, situated in the range from 15° to 37° C.

The assay technique according to the invention, which is advantageously based on the invisibility/visibility change in submicron particles due to agglutination, differs from the teaching of the technical solutions of the prior art referred to above.

DETAILED DESCRIPTION OF THE INVENTION

Figure 1:
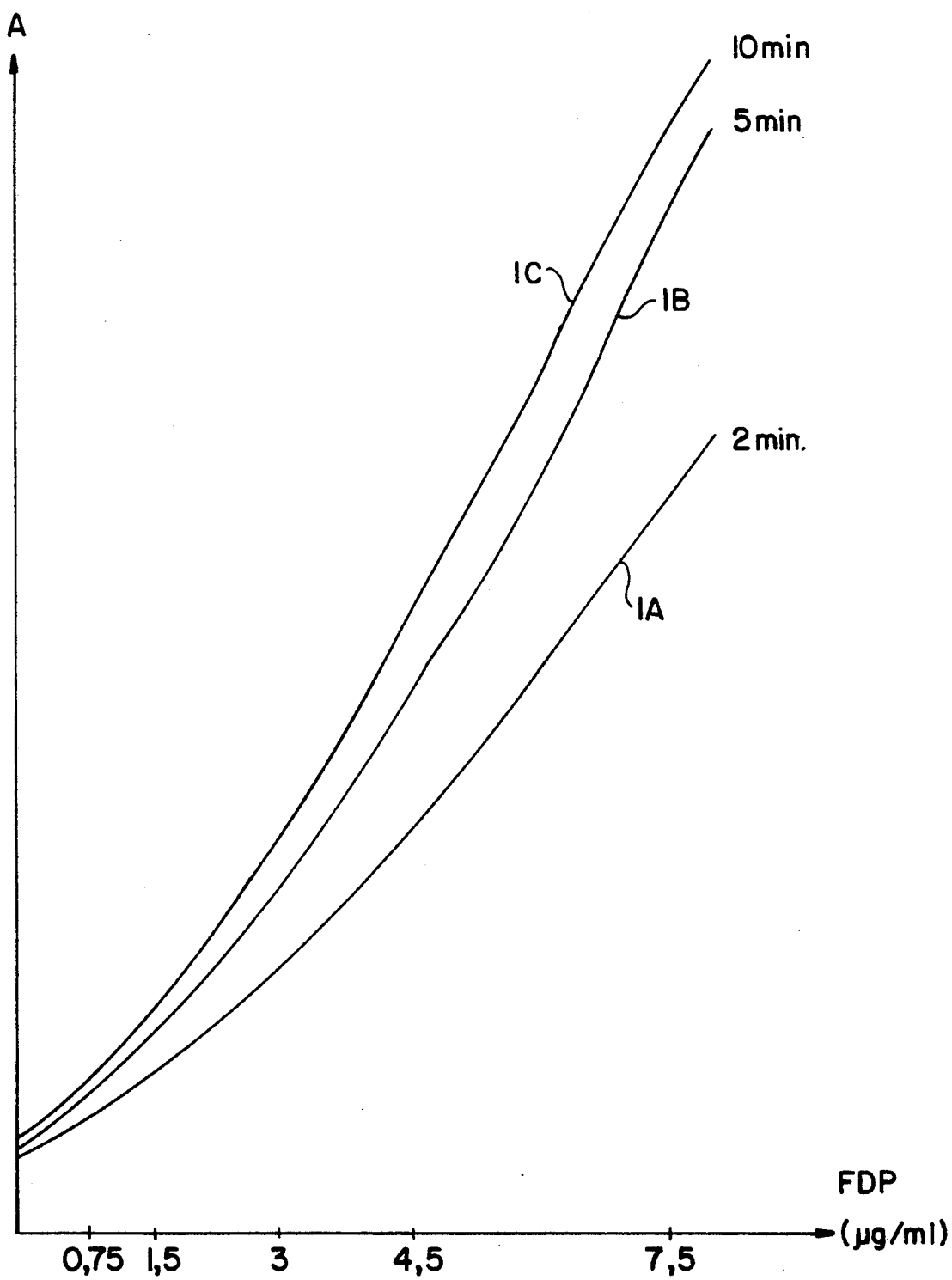

According to the invention, the expressions "invisible particles" and "visible particles" are understood as meaning that, on the one hand, the so-called invisible or transparent particles neither absorb nor diffuse electromagnetic radiation, such as light, passing through the medium containing said particles, without substantial deviation of said radiation, and on the other hand, the so-called visible particles absorb and/or diffuse said electromagnetic radiation.

The expression "immunological substance" or "immunological material" is understood as meaning any substance, selected from the group consisting of antigens and antibodies, which is to be bound to the microparticles by covalency or adsorption.

The term "ligand" is understood here as meaning the antigen or antibody bound to each latex particle by covalency or adsorption.

The expression "immunological reagent" is understood as meaning the whole consisting of the latex particles and the immunological substance, selected from antibodies and antigens, which is bound to each of said particles by adsorption, said latex particles, coated with said immunological material, being stabilized by means of a stabilizing material.

The term "substance" or "corresponding compound" (homologous, complementary and/or conjugate compound) for an antibody (or antigen) is understood as meaning the antigen or antibody, respectively, which reacts with the antibody or antigen, respectively, of the immunological reagent.

Here the term "antigen" denotes any antigen in the proper sense, as well as any substance from which it is possible to generate an antibody; among the substances capable of generating antibodies, there may be mentioned especially haptens, peptides, drugs containing at least one peptide fragment, alkaloids and, in general, any substance having an immunological structure.

As indicated above, the choice of latex is important for carrying out the binding method and the assay method according to the invention. It is recommended more particularly to use acrylic latex particles based on polybutyl methacrylate, whose mean diameter is less than or equal to 100 nm, said latex containing a molar quantity of butyl methacrylate units greater than 50%, having a density of 0.9 to 1.4 g/cm$^3$ and containing from 100 to 450 microequivalents of COOH groups per gram of latex.

More precisely, the acrylic latex used will be a copolymer essentially consisting of styrene units and butyl methacrylate units in a molar ratio styrene units/butyl methacrylate units of 40/60 to 45/55.

Even more advantageously, it is recommended to use a copolymer essentially consisting of styrene units and butyl methacrylate units in a molar ratio styrene units/butyl methacrylate units of 42/58 to 43/57, having a density of 1.0 to 1.1 g/cm$^3$ and containing from 250 to 300 microequivalents of COOH groups per gram of latex.

Of the latex particles which are suitable according to the invention, it is preferred to use those which have a diameter (d) of 67 nm and a density of 1.0 to 1.1 g/cm$^3$ and which consist of a styrene/butyl methacrylate copolymer, manufactured by RHONE-POULENC, in which the molar ratio styrene units/butyl methacrylate units is 42.4/57.6 and which contains from 250 to 300 microequivalents of COOH groups per gram of latex.

As indicated above, it is essential for the latex particles useful according to the invention to have a mean diameter (d) which is less than or equal to 100 nm, preferably between 1 and 100 nm and most preferably in the range from 5 to 100 nm.

The electromagnetic radiation used according to the invention to assess the variation in agglutination during the reaction of the immunological reagent with its conjugate must then have a wavelength ($\lambda$) which is distinctly greater than the mean diameter (d) of the latex particles. Advantageously, said wavelength will be in the range from 300 to 1000 nm (especially 400 to 700 nm). As indicated above, the ratio $\lambda/d$ will be greater than or equal to 5.

It is also important for the latex to have a functionality which reacts with the immunological substance. Latices which are suitable here are those comprising a COOH functionality, i.e. actual COOH groups or, depending on the pH of the medium, COO— or COOR' groups, where R' is a blocking group conventionally used in the field of immunology, which can be in particular a $C_1$-$C_4$ alkyl, phenyl or benzyl group, the preferred groups R' here being $C_1$-$C_4$ alkyl groups such as methyl, ethyl, isopropyl, t-butyl or s-butyl.

In practice, the reactive groups of the functionality which reacts with the immunological substance will represent approximately 100 to 450 microequivalents (referred to here as COOH groups for the sake of convenience) per gram of latex.

According to the invention, the immunological material is bound to the submicron latex particles by covalency or adsorption. Covalent binding differs from binding by adsorption in that the COOH functionality, as defined above, is, in the case of covalent binding, activated or sensitized by a carbodiimide compound (which is advantageously soluble in the biological preparation medium).

For covalent binding, the contacting process of section (A) is carried out by a method which comprises bringing said immunological material into contact, for at least 10 minutes, in an aqueous medium buffered to a pH of 4-10 and having an ionic strength of 0.01 to 0.5, with said latex particles in which the active COOH sites have been sensitized beforehand by means of a carbodiimide compound, and then adding an excess of a stabilizing material to block the active sites which are still free on said latex particles.

As a variant, covalent binding can comprise, prior to said contacting process, reacting the active sites of said latex particles (activated or sensitized beforehand by reaction with said carbodiimide compound) with a difunctional chain-extending compound, in an aqueous medium buffered to pH 4-10 and having an ionic strength of 0.01 to 0.5, at a temperature of 40°-60° C., for at least 10 minutes.

Thus the latices with reactive COOH functionality according to the invention can be used either direct for covalent coupling of the ligand by chemical reaction, or after lateral chain extension by means of a difunctional arm. Among the difunctional compounds which are useful for creating the difunctional arm or bridge and which are suitable according to the invention, there may be mentioned diamines and amino acids containing an amino group in the terminal position relative to the carboxyl group, such as, for example, $\epsilon$-aminocaproic acid; this arm or bridge is then activated for covalent coupling.

The major characteristic of the latices is their ability to form stable suspensions which can be destabilized specifically under defined conditions, namely the antigen/antibody reaction in the case in question. According to the invention, the particles sensitized by an antigen or antibody, for example a hapten, retain the properties inherent in the latex and that of the coupled immunological substance. Said particles remain monodisperse during storage and aggregate only in the presence of the complementary component of the ligand/antiligand system.

With regard to the reactive functionality, the presence of functional groups, such as COOH or others mentioned above, on the surface of the latex particles permits covalent coupling with the functional groups of the ligand. Without implying a limitation, COOH/NH$_2$ functional couples will advantageously be used according to the invention. Of course, other combinations of functional couples known in the art can also be envisaged.

Non-limiting examples of covalent coupling are given below by way of information:

Activation of the COOH groups of the latex with a water-soluble carbodiimide (for example EDAC, morphocarbodiimide or any other soluble carbodiimide) reacting with the NH$_2$ groups of the ligand, at a pH of between 4 and 10, in a medium devoid of free amino groups; activation can be effected in two stages, with elimination of the excess coupling reagent (preferred method), or direct in a single stage; the ligand is then added in the appropriate proportion, after which the latex is saturated and stabilized.

Activation of the COOH groups of the latex with a carbodiimide and grafting of an intermediate arm: in a first stage, the latices activated by the carbodiimide are "derivatized" with an excess of a diamine (in this technique, an aliphatic diamine containing from 2 to 10 carbon atoms is normally used) in order to keep the ligand away from the surface, making it more reactive, and to create NH$_2$ groups; the "derivatized" particles obtained in this way are then activated with glutaraldehyde (of which the excess is removed) or carbodiimide; after activation, said particles react with the NH$_2$ or COOH groups of the ligand.

The use of latices with reactive functionality which contain other reactive groups affords interesting possibilities for covalent coupling:

carboxylated latex (COOH) activated by a carbodiimide or a 2-ethoxy-1-(2H)-quinolinecarboxylate, especially ethyl 2-ethoxy-1-(2H)-quinolinecarboxylate (EEDQ), and latex with ester groups (COOR'') activated by glutaraldehyde.

For binding by covalency or adsorption, the stabilization of section (B) is carried out during or after the contacting process of section (A). In other words, the stabilizing material provided for in section (B) can be introduced into the biological reaction medium during the contacting process (A) or thereafter. In general, said stabilizing material is preferably introduced after said contacting process has been carried out; in the case of covalent binding, it is possible to introduce said stabilizing material into said contacting medium provided said stabilizing material does not contain any reactive $NH_2$ groups.

To complete the stabilization, the addition of the stabilizing material can be followed by the introduction of a ballast consisting of a protein-type or polyhydroxylated material, which is particularly useful for lyophilizing the immunological reagent according to the invention.

As a variant, such a ballast can be used before the process of section (A), for covalent binding of the immunological material to the latex particles, in order to form a molecular binding layer (albumin or an organic polymer such as polylysine) between the latex and the ligand.

In the mode of sensitization of the latex particles and binding of the ligand by covalency or adsorption, the experimental conditions, namely the pH, the ionic strength, the volume, the temperature, the duration and the concentration of the ligand, are adjusted according to the nature of the product to be assayed, so as to ensure a perfect stability of the particulate immunological reagent in an appropriate biological medium, a maximum reactivity and an effective reproducibility, and an excellent preservation of the immunological reagent on storage (no substantial degradation or inactivation of said reagent was observed after a storage period of 12-18 months at +4° C.).

From a practical point of view, it is found that, irrespective of the buffer, increasing the pH and ionic strength results in a stabilization of the immunological reagent on the one hand and causes a proportional decrease in the reactivity on the other.

It is for this reason that an overall adjustment is recommended for the preparation of the immunological reagent, which makes it possible to mitigate the above-mentioned paradoxical feature and which involves the use of an aqueous liquid medium comprising water and a buffer, having a pH in the range from 4 to 10 (advantageously 6-9 and preferably 8.2-8.5), having an ionic strength in the range from 0.01 to 0.5 and containing, if appropriate, for stabilizing the latex particles, an inert protein-type or polyhydroxylated ballast incorporated after the stabilization of section (B).

In practice, the reaction of the immunological reagent with the complementary or conjugate substance will be carried out in an aqueous liquid medium having a pH of 4-10, especially a pH of 5-9, and an ionic strength of 0.01-0.5 and containing, if appropriate, a polymeric alcohol and/or a substance selected from inert proteins and amino acids.

The assay method recommended according to the invention, which involves a reaction of the antigen/antibody type, consists in (1) bringing (i) particles whose mean diameter (d) is less than or equal to 100 nm and which are coated with an immunological substance selected from antigens and antibodies and bound to each of said particles by covalency or adsorption, those active sites of each of said particles which are not bound to said immunological substance being essentially blocked by a stabilizing material selected from the group consisting of hydroxylated substances containing one or, preferably, several OH groups per molecule, protein-type substances, peptide-type substances, amino acids, polyose-type substances containing one or more carboxylic acid and/or carboxylate groups, polyvinylpyrrolidone, analogs thereof and mixtures thereof, into contact with (ii) a complementary or conjugate substance for said immunological substance, in an aqueous liquid medium having a pH in the range from 4 to 10 and an ionic strength in the range from 0.01 to 0.5, and (2) assessing the change in agglutination by exposure to radiation with a wavelength ($\lambda$) in the range from 300 to 1000 nm (especially 400-700 nm) and such that the ratio $\lambda/d$ is greater than or equal to 5.

In this method, either the actual agglutination or the inhibition of agglutination is assessed.

The temperature which is recommended for carrying out this method is in the range from 4° to 60° C. and preferably 15° to 37° C.

The assay will preferably be performed by turbidimetry. Assay by turbidimetry has the advantage that it can easily be used by any laboratory equipped only with a photometer or spectrophotometer (working at a wavelength of between 300 and 1000 nm) or equipped with a sophisticated automatic apparatus (of the centrifugal analyzer type such as the "Cobas Bio" analyzer).

The assay can also be performed by nephelometry or particle counting, but the use of these methods is more restrictive on account of the cost of the apparatus.

The sensitivity of the assay according to the invention is generally at least 100 ng/ml. In certain cases, the sensitivity threshold, especially for nephelometry, may be lower and equal to at least 10 ng/ml.

According to an advantageous mode of carrying out the method, afforded by the invention, the assay time will generally be short and especially between 30 and 600 s.

Such an assay is applicable to the quantitative determination on the one hand of antigens and antibodies and on the other hand of any substances capable of generating antibodies, such as haptens, peptides, drugs containing at least one peptide fragment, and alkaloids, in various biological media such as plasma, serum, urine, cerebrospinal fluid and biological extracts, for various sectors of the art, such as animal health, human health, the agri-foodstuffs sector, the environment and the like.

The best mode of carrying out the invention consists in carrying out the contacting process of section (A) in an aqueous biological medium having a pH of 6-9 or, preferably, 8.2-8.5 (in particular in a glycine buffer of pH 8.35) and having an ionic strength of 0.01-0.5. The duration of the contacting process of section (A) is at least 10 minutes for covalent binding of the immunological material and at least 60 minutes for binding of said immunological material by adsorption.

According to this best mode of carrying out the invention, 100 parts by weight of latex particles are brought into contact, in accordance with section (A), with 1 to 50 or, preferably, 2 to 20 parts by weight of immunological material, after which 10 to 100 parts by weight of stabilizing material are used per 100 parts by weight of latex particles used in said contacting process.

Again according to this best mode, the stabilizer is added, after the contacting process of section (A), in a biological medium which is identical or similar to that of said contacting process.

For carrying out the assay method, it is recommended to use an aqueous biological medium which is identical or similar to that of the contacting process of section (A).

Further advantages and characteristics of the invention will be understood more clearly from the following description of Examples, which in no way imply a limitation but are given by way of illustration.

In these Examples, Examples 1–4 relate to an immunological reagent in which the immunological material is covalently bound to the submicron latex particles, and Examples 5–8 relate to an immunological reagent in which the immunological material is bound to the submicron latex particles by adsorption.

EXAMPLE 1

Preparation of the immunological reagent

The latex used is based on polybutyl methacrylate and more precisely on a styrene/butyl methacrylate copolymer in which the molar ratio styrene units/butyl methacrylate units is 42.4/57.6, with a density of 1.02 g/cm$^3$, in the form of beads with a diameter of 67 nm, manufactured by RHONE-POULENC. The reactive functionality of this latex (referred to hereafter as "latex 1") consists of COOH and/or COOR" groups, depending on the pH of the medium, the total proportion of reactive COOH and COOR" groups representing a quantity of 250 to 300 microequivalents per gram of latex.

The covalent binding of the immunological substance (i.e. the antigen or antibody) is effected in two steps. Prior activation of the carboxyl and/or carboxylate groups of the latex with a carbodiimide is followed by coupling of the ligand. 5 mg of carbodiimide are added to 1 ml of 10% w/v latex. After incubation at 50° C. or room temperature (for 10 minutes to 2 hours), the latex beads are washed several times and then brought into contact with 1 to 30 mg of dilute antigen or antibody (preferably 5 to 10 mg) for 10 to 30 minutes, in an aqueous biological buffer (glycine buffer at pH 8.35), the ionic strength of the contacting medium being 0.01–0.5. An amino substance is finally added, in order to saturate the free sites, in a volume which enables the reagent to be used direct (final concentration: 0.75% w/v).

EXAMPLE 2

Assay of FDP in serum

The following are introduced successively into the measuring cell: 15 μl of standard or assay sample and 500 μl (for spectrophotometry) or 200 μl (for the Cobas Bio) of latex beads coated with an antibody and diluted in a reaction buffer (final concentration: 0.075%) [said beads being prepared according to Example 1 from an anti-FDP antibody (generated by a method known per se from one or more FDP—fibrinogen degradation products)]. The results are read off at 600 nm, either manually on a spectrophotometer after a reaction time of 60 to 600 s or automatically on a "Cobas Bio" after a reaction time of 30 to 180 s, or any other kinetic measurement. The reaction rate also makes it possible to read off kinetic results between 60 s and 600 s manually FIG. 1) or between 30 s and 600 s on a "Cobas Bio" analyzer FIGS. 2a and 2b). The zone effect is observed for concentrations above 500 μg/ml in the sample. An additional predilution makes it possible to eliminate any risk of error due to excess antigen. The detection threshold in the reaction medium is 100 ng/ml.

FIG. 1 gives the calibration curves 1A, 1B and 1C for reaction times of 2, 5 and 10 minutes, respectively, in the system absorbance A (on the ordinate)/final FDP concentration (expressed in μg/ml on the abscissa), under exposure to radiation of 600 nm.

Figure 2A:
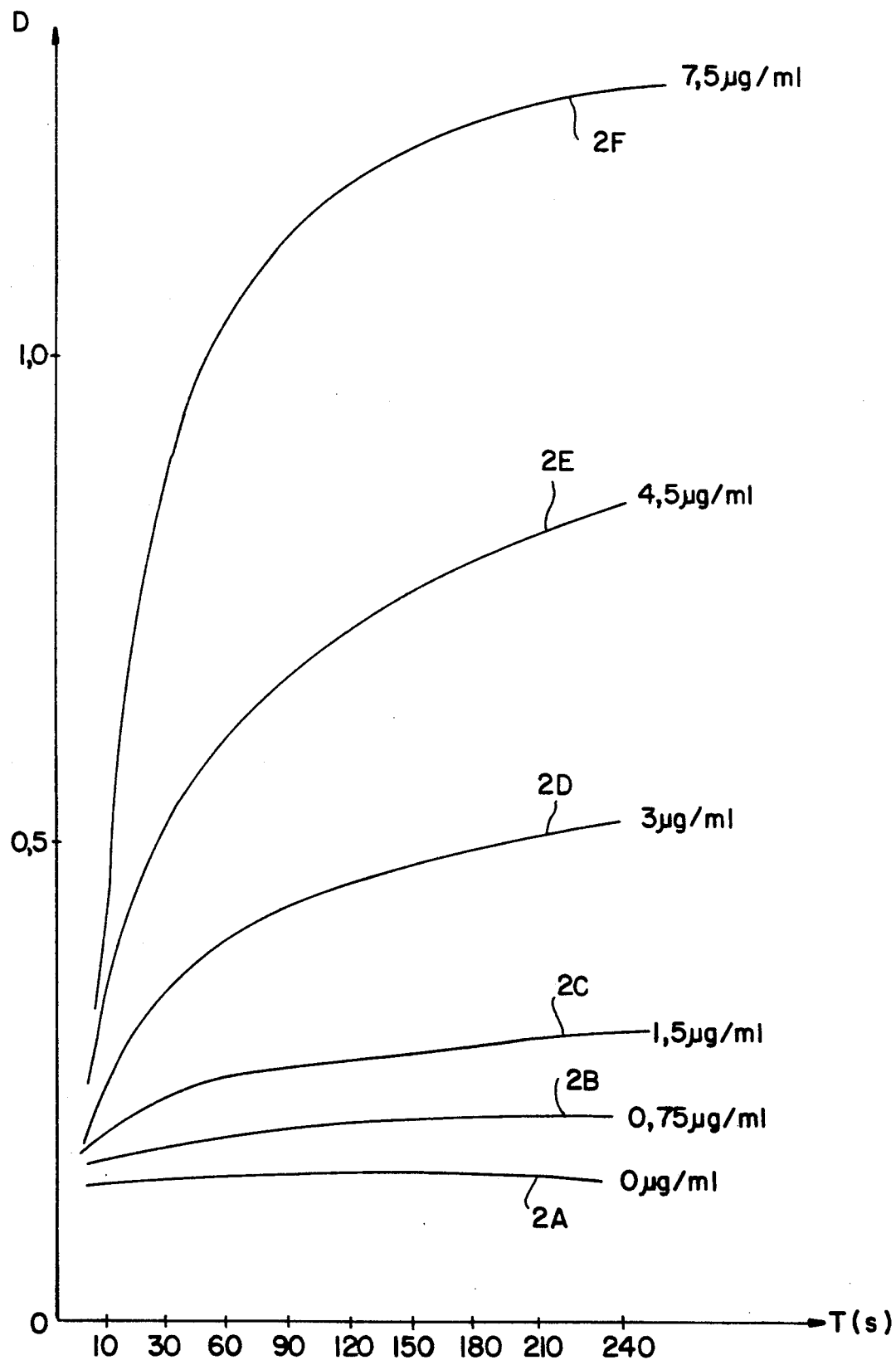

FIG. 2a gives the curves of the kinetics obtained in the assay of FDP in the system optical density D (on the ordinate)/reaction time T (expressed in seconds on the abscissa) for final FDP concentrations of 0 (curve 2A), 0.75 (curve 2B), 1.5 (curve 2C), 3 (curve 2D), 4.5 (curve 2E) and 7.5 μg/ml (curve 2F), under exposure to radiation of 600 nm, by means of a "Cobas Bio" analyzer.

Figure 2B:
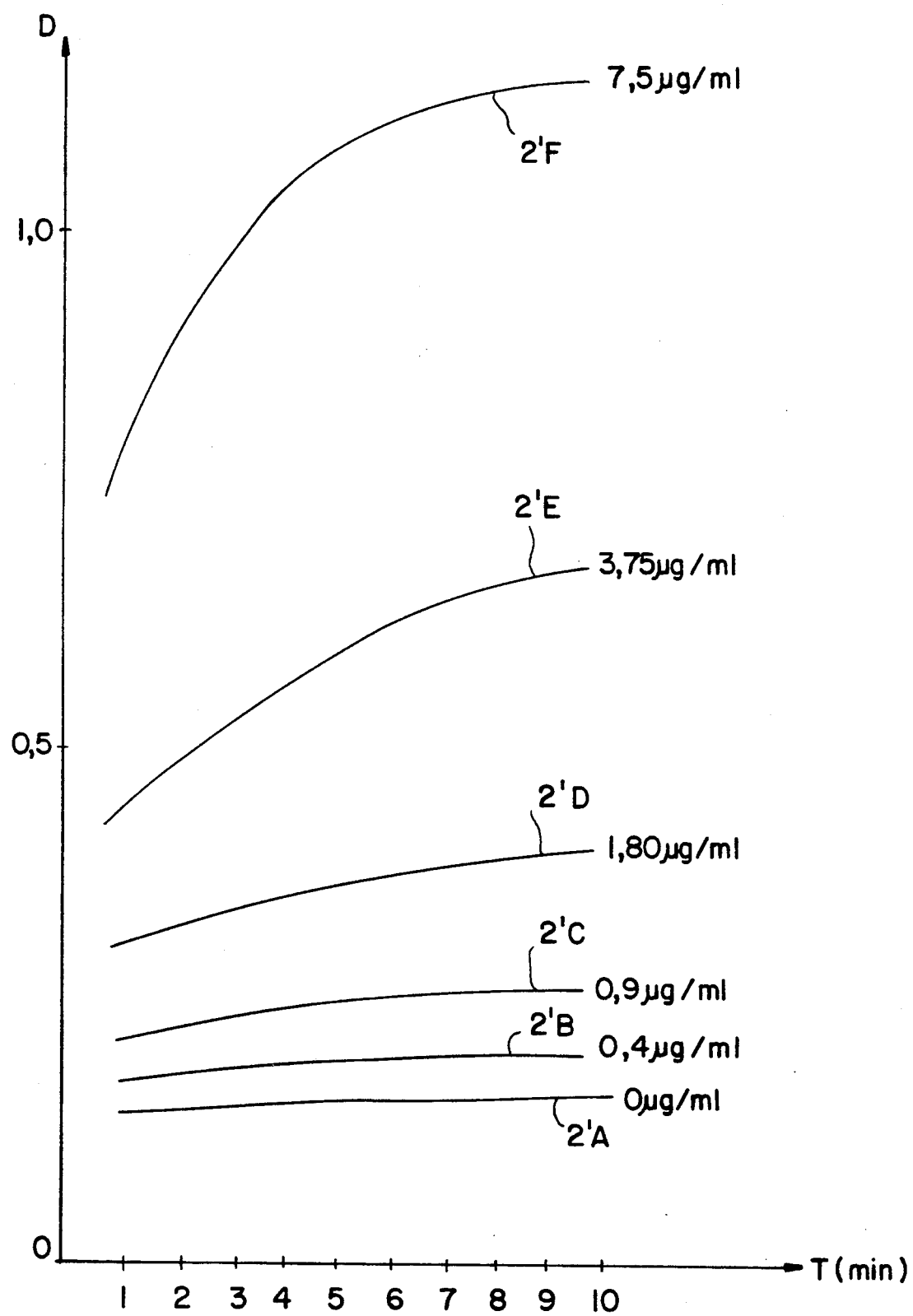

Likewise, FIG. 2b gives the curves of the kinetics obtained in the assay of FDP in the system optical density D (on the ordinate)/reaction time T (expressed in minutes on the abscissa) for final FDP concentrations of 0 (curve 2'A), 0.4 (curve 2'B), 0.9 (curve 2'C), 1.8 (curve 2'D), 3.75 (curve 2'E) and 7.5 μg/ml (curve 2'F), under exposure to radiation of 600 nm, by means of a "Cobas Bio" analyzer.

EXAMPLE 3

Direct assay of antithrombin III (AT III)

50 μl of standard or sample, prediluted 80-fold, are mixed with the latex-antibodies [prepared according to Example 1 from anti-AT III] diluted to a volume of 500 μl in the reaction buffer (final concentration: 0.075% w/v).

The results are read off at 600 nm after a reaction time of 2 to 10 minutes. The calibration range is between 0 and 200% of plasma AT III, which corresponds to values of between 0 and 3.7 μg/ml in the reaction medium (FIG. 3).

Figure 3:
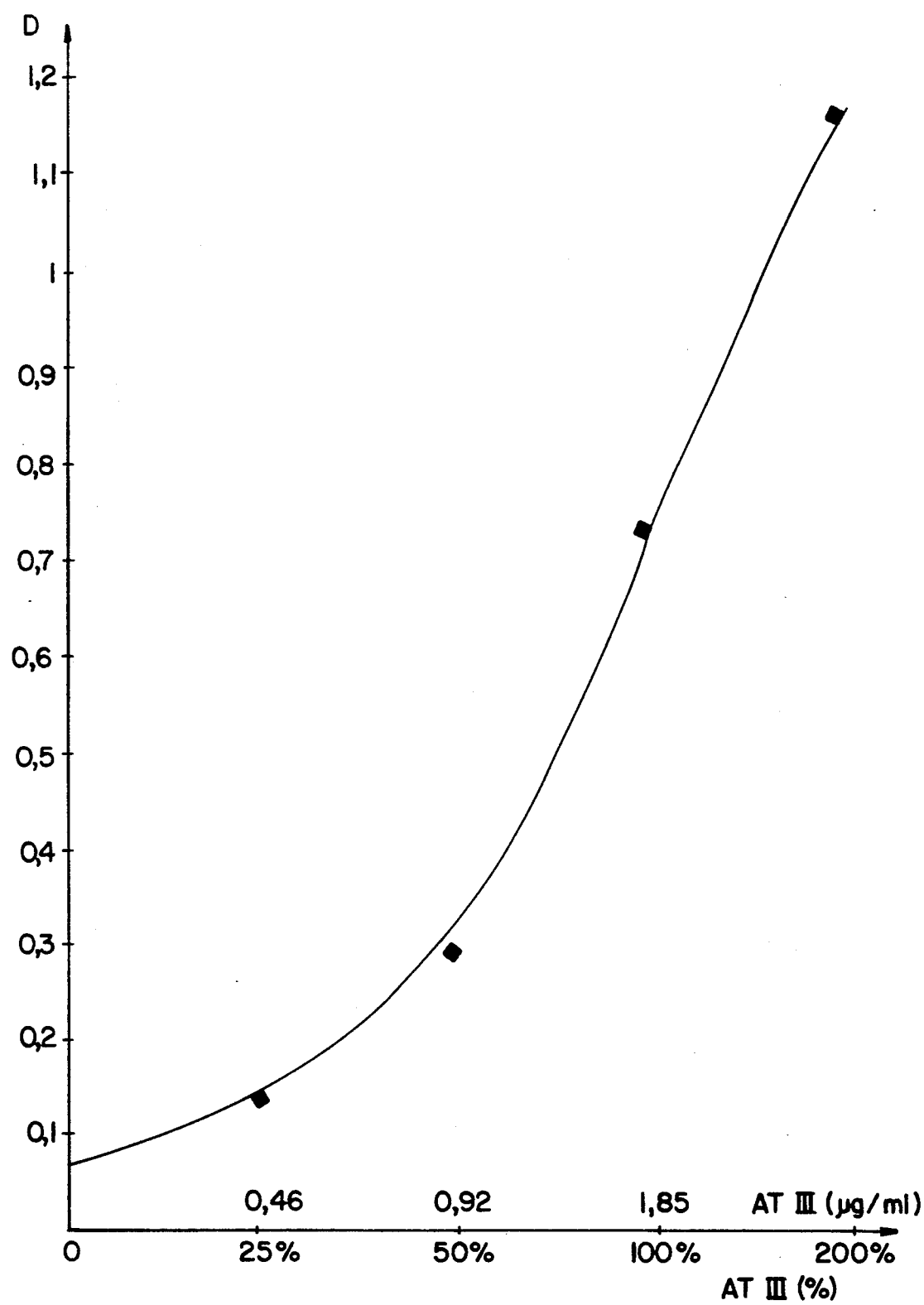

FIG. 3 gives the calibration curve at 600 nm for plasma AT III (on the abscissa: final concentrations of AT III in μg/ml and of corresponding plasma AT III expressed in %; on the ordinate: optical density D) after incubation for 5 minutes.

EXAMPLE 4

Indirect assay of FDP

200 μl of antibody, in the present case an anti-FDP, and 600 μl of prediluted free FDP are first introduced into the measuring cell. The reaction is then started by adding the latex beads sensitized by FDP (at 0.75%) [prepared according to Example 1 from FDP bound to said beads] to give a final volume of 1 ml.

The FDP concentrations to be assayed, resulting in an inhibition of the reaction, are expressed as a function of the variation in optical density or absorbance measured at 600 nm on a spectrophotometer.

Figure 4:
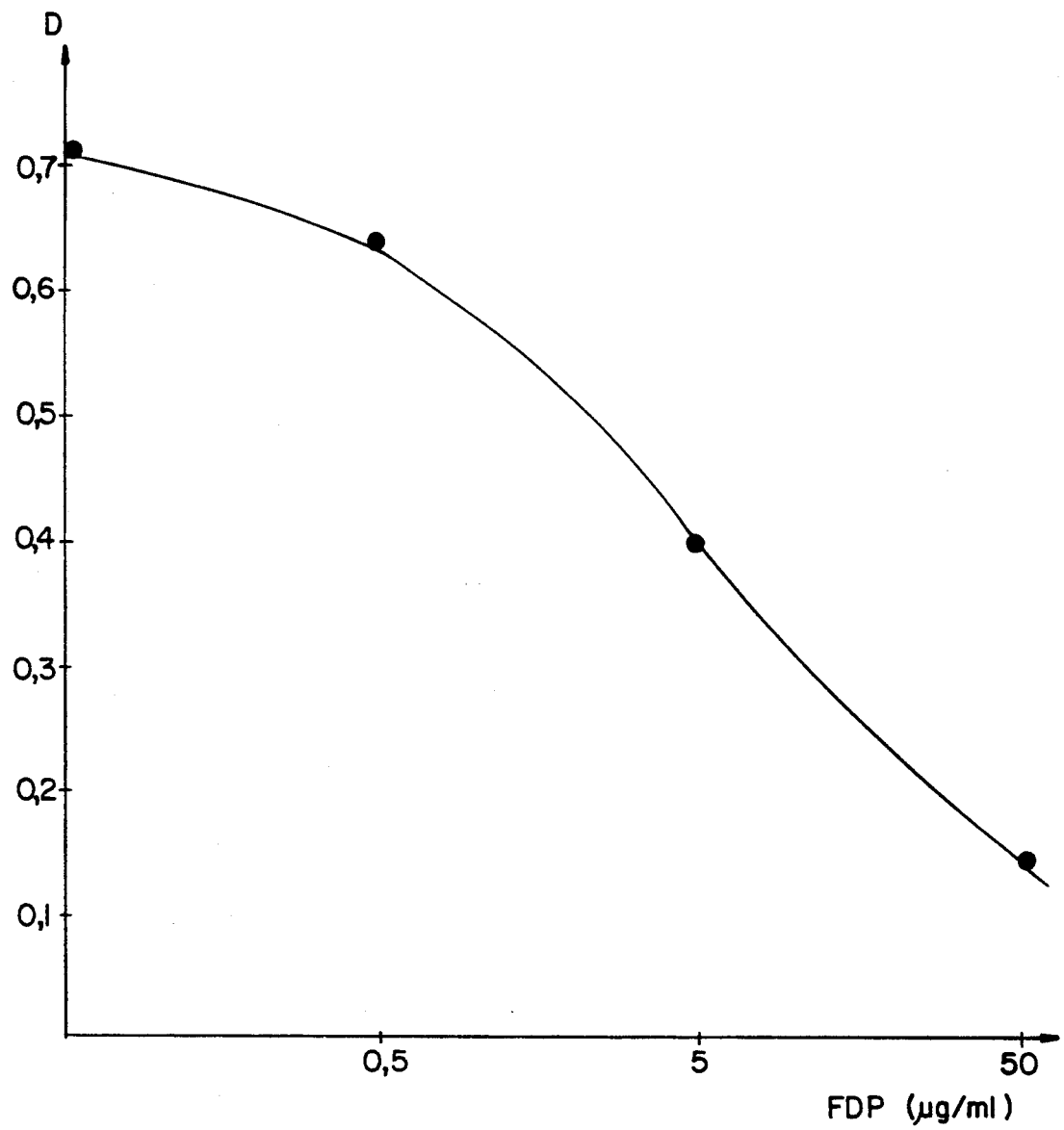

FIG. 4 below gives the agglutination inhibition curve for the latex/FDP reagent in the system optical density D (on the ordinate)/FDP concentration (expressed in μg/ml on the abscissa) at 600 nm.

EXAMPLE 5

Preparation of the immunological reagent

The latex used is latex 1 of Example 1, in the form of beads with a diameter of 67 nm, the reactive functionality of this latex representing, as indicated in Example 1, a quantity of 250 to 300 microequivalents of carboxyl groups per gram of latex.

Binding of the immunological substance (i.e. the antigen or antibody) by adsorption is effected on the surface of the polymeric material of the particles. 100 mg (1 ml at a concentration of 10% w/v) of submicron particles of latex 1 are brought into contact with 1 to 50 mg (preferably 2 to 20 mg) of high-purity antibody (or antigen) in a glycine buffer at pH 8.35, the biological adsorption medium having an ionic activity of 0.01–0.5. The mixture is incubated at 56° C. for 1-24 h.

The submicron particles to which the immunological substance has been bound are rinsed; then, after suspension in the same glycine buffer at pH 8.35, 20 to 40 mg of a polyhydroxylated material, in this case preferably diethylene glycol, ethylene glycol, glycerol or PEG, are added; the mixture is then incubated at 56° C. for 1-24 h.

The resulting suspension is then diluted to the use dilution (in this case 0.075% w/v by means of the glycine stabilizing buffer containing said polyhydroxylated material (in this case diethylene glycol, ethylene glycol, glycerol or PEG) and albumin.

EXAMPLE 6

Assay of FDP in serum

The following are introduced successively into the measuring cell: 15 µl of standard or assay sample and 500 µl (for spectrophotometry) or 200 µl (for the Cobas Bio) of latex beads coated with an antibody and diluted in a reaction buffer (final concentration: 0.075%) [said beads being prepared according to Example 5 from an anti-FDP antibody generated by a method known per se from one or more FDP (fibrinogen degradation products)]. The results are read off at 600 nm, either manually on a spectrophotometer after a reaction time of 60 to 600 s or automatically on a "Cobas Bio" after a reaction time of 30 to 180 s, or any other kinetic measurement. The reaction rate also makes it possible to read off kinetic results between 60 s and 600 s manually (FIG. 5) or between 30 s and 600 s on a "Cobas Bio" analyzer (FIGS. 6a and 6b). The zone effect is observed for concentrations above 500 µg/ml in the sample. An additional predilution makes it possible to eliminate any risk of error due to excess antigen. The detection threshold in the reaction medium is 100 ng/ml.

Figure 5:
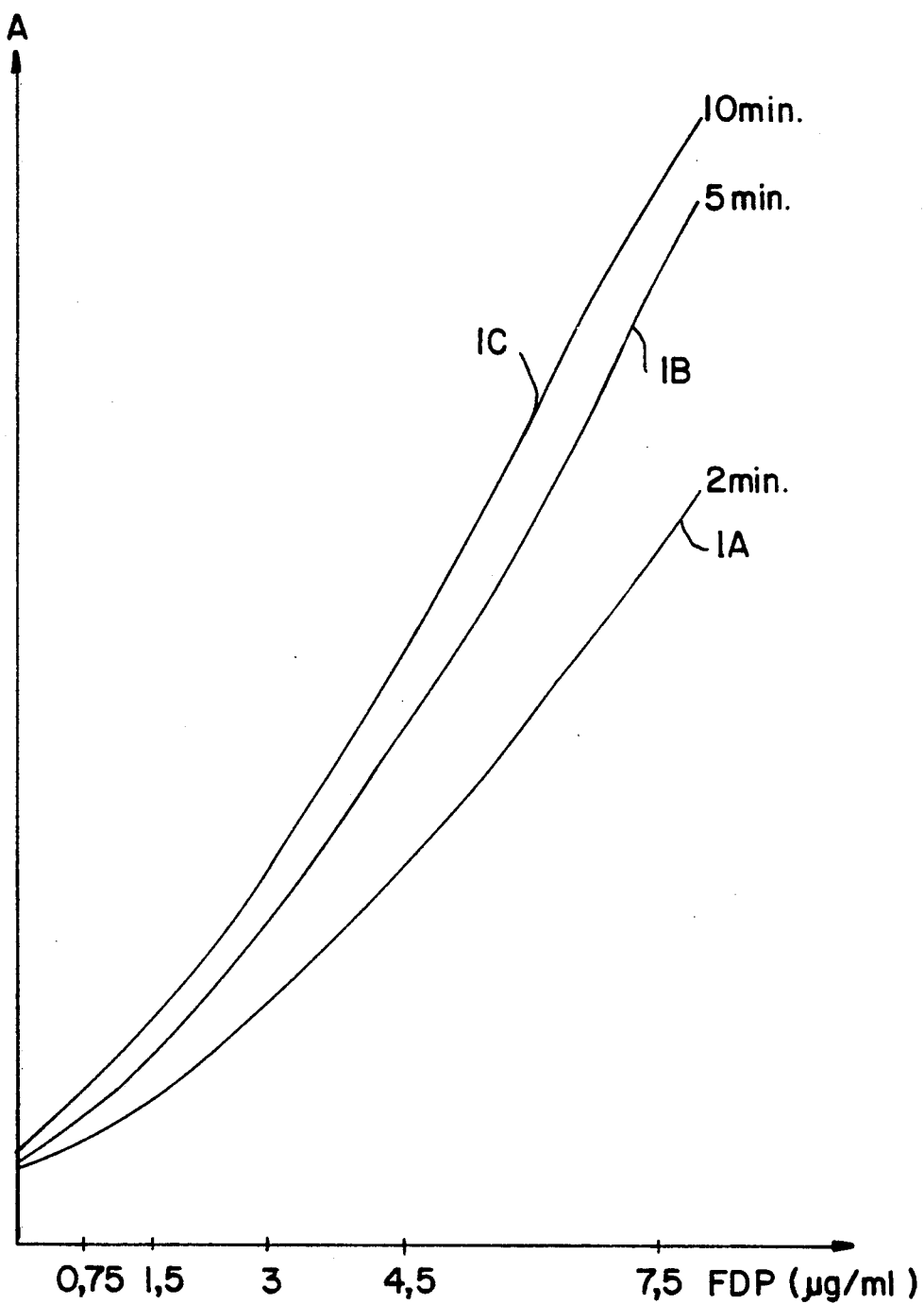
Figure 6A:
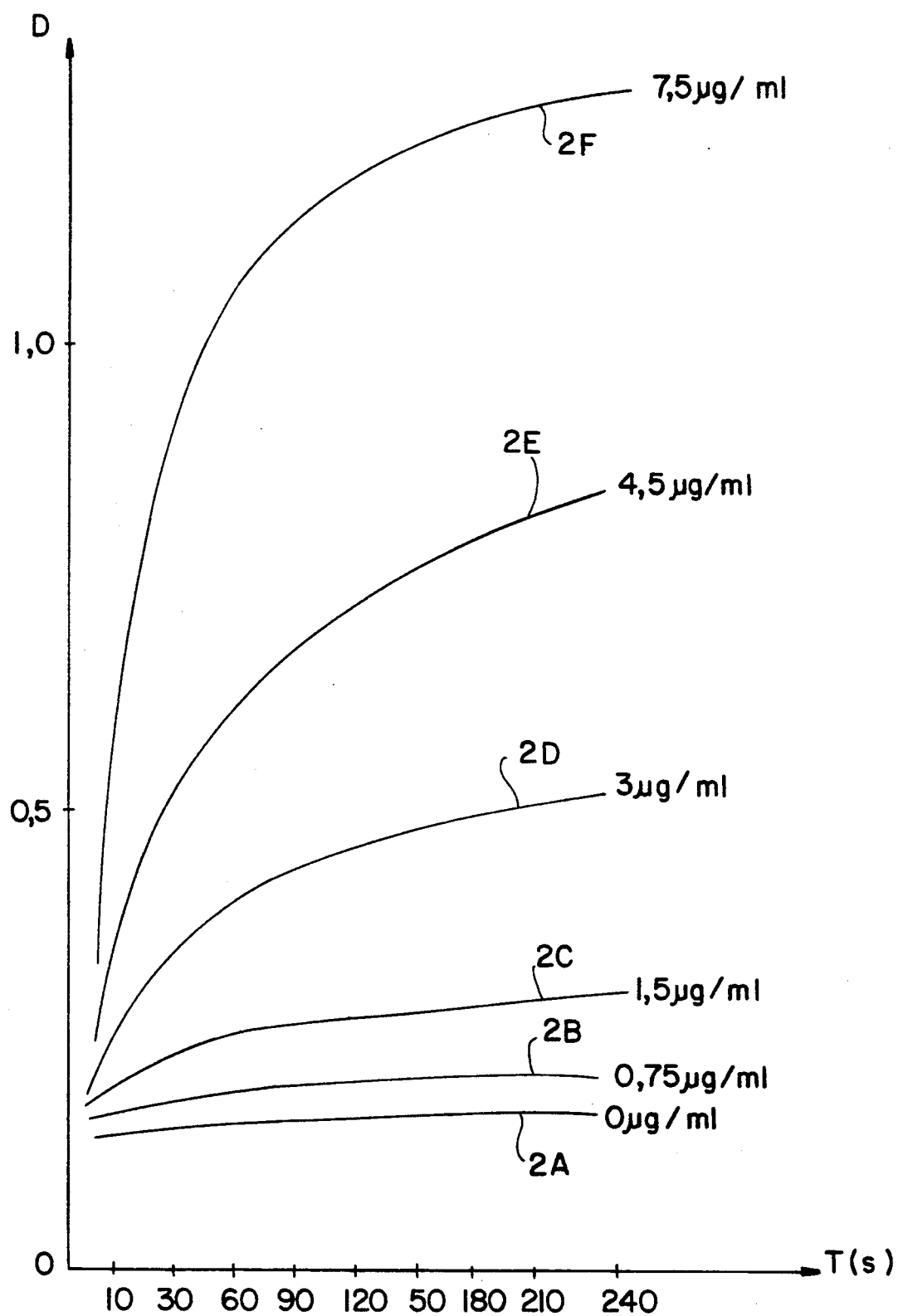
Figure 6B:
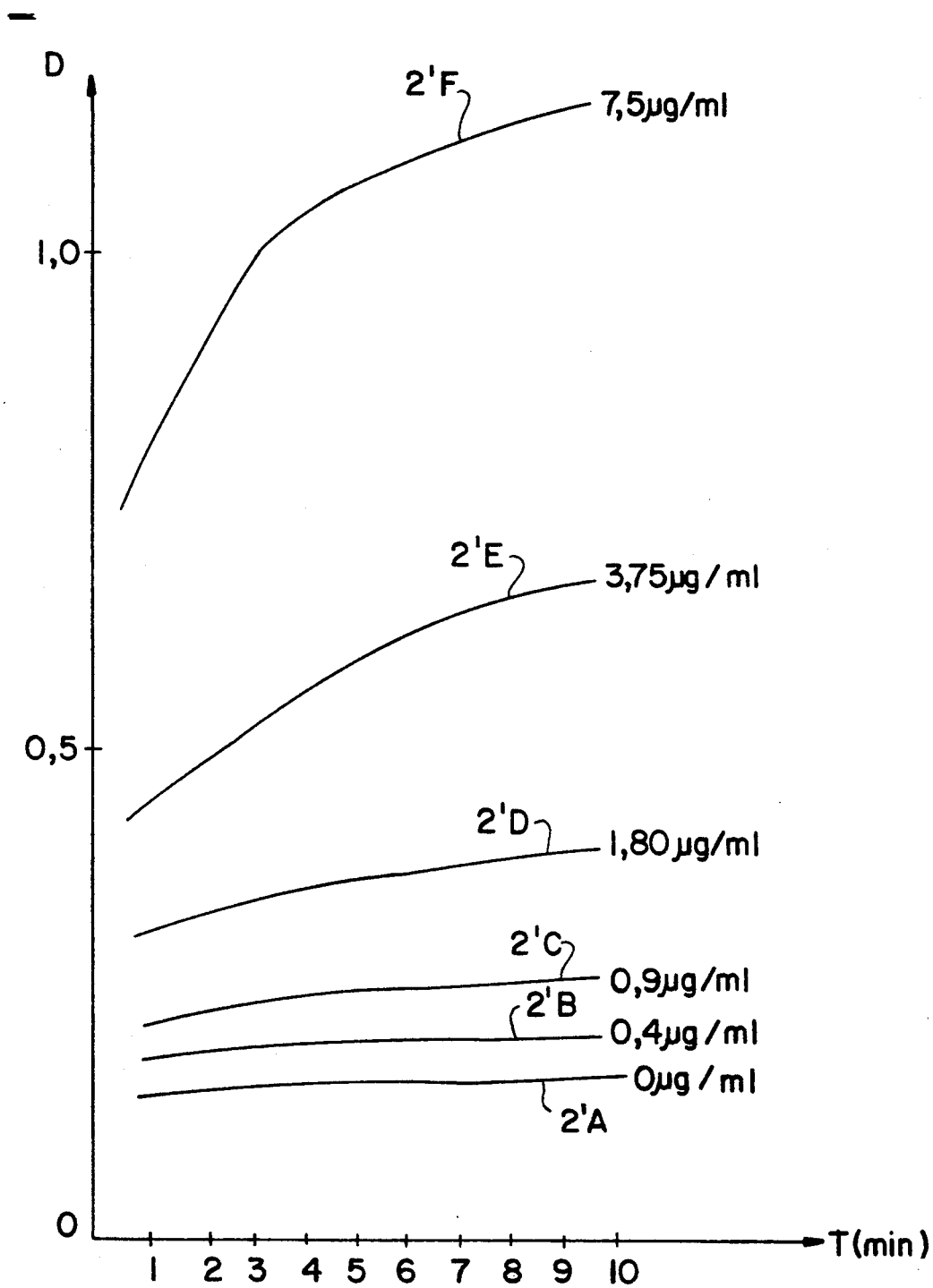

FIG. 5 gives the calibration curves 1A, 1B and 1C for reaction times of 2, 5 and 10 minutes, respectively, in the system absorbance A (on the ordinate)/final FDP concentration expressed in µg/ml (on the abscissa), under exposure to radiation of 600 nm.

FIG. 6a gives the curves of the kinetics obtained in the assay of FDP in the system optical density D (on the ordinate)/reaction time T expressed in seconds (on the abscissa) for final FDP concentrations of 0 (curve 2A), 0.75 (curve 2B), 1.5 (curve 2C), 3 (curve 2D), 4.5 (curve 2Ee and 7.5 µg/ml (curve 2F), under exposure to radiation of 600 nm, by means of a "Cobas Bio" analyzer.

Likewise, FIG. 6b gives the curves of the kinetics obtained in the assay of FDP in the system optical density D (on the ordinate)/reaction time T expressed in minutes (on the abscissa) for final FDP concentrations of 0 (curve 2′A), 0.4 (curve 2′B), 0.9 (curve 2′C), 1.8 (curve 2′D), 3.75 (curve 2′E) and 7.5 µg/ml (curve 2′F), under exposure to radiation of 600 nm, by means of a "Cobas Bio" analyzer.

EXAMPLE 7

Direct assay of antithrombin III (AT III)

50 µl of standard or sample, prediluted 80-fold, are mixed with the latex-antibodies [prepared according to Example 5 from anti-AT III] diluted to a volume of 500 µl in the reaction buffer (final concentration: 0.075% w/v).

The results are read off at 600 nm after a reaction time of 2 to 10 minutes. The calibration range is between 0 and 200% of plasma AT III, which corresponds to values of between 0 and 3.7 µg/ml in the reaction medium (FIG. 7).

Figure 7:
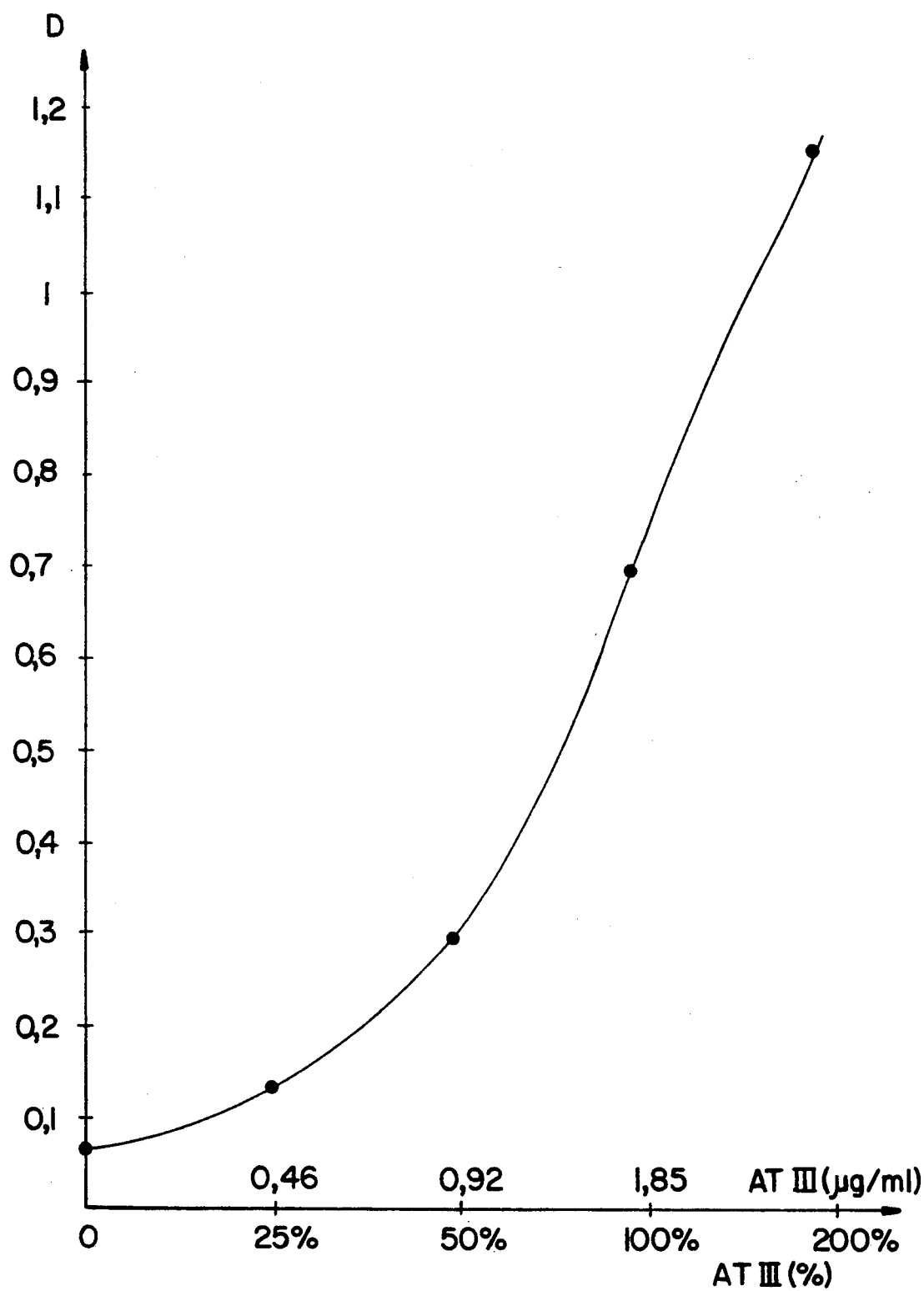

FIG. 7 gives the calibration curve at 600 nm for plasma AT III (on the abscissa: final concentrations of AT III in µg/ml and of corresponding plasma AT III expressed in %; on the ordinate: optical density D) after incubation for 5 minutes.

EXAMPLE 8

Indirect assay of FDP

200 µl of anitbody, in the present case an anti-FDP, and 600 µl of prediluted free FDP are first introduced into the measuring cell. The reaction is then started by adding the latex beads sensitized by FDP (at 0.75%) [prepared according to Example 5 by adsorption of FDP on to said beads] to give a final volume of 1 ml.

The FDP concentrations to be assayed, resulting in an inhibition of the reaction, are expressed as a function of the variation in optical density or absorbance measured at 600 nm on a spectrophotometer.

Figure 8:
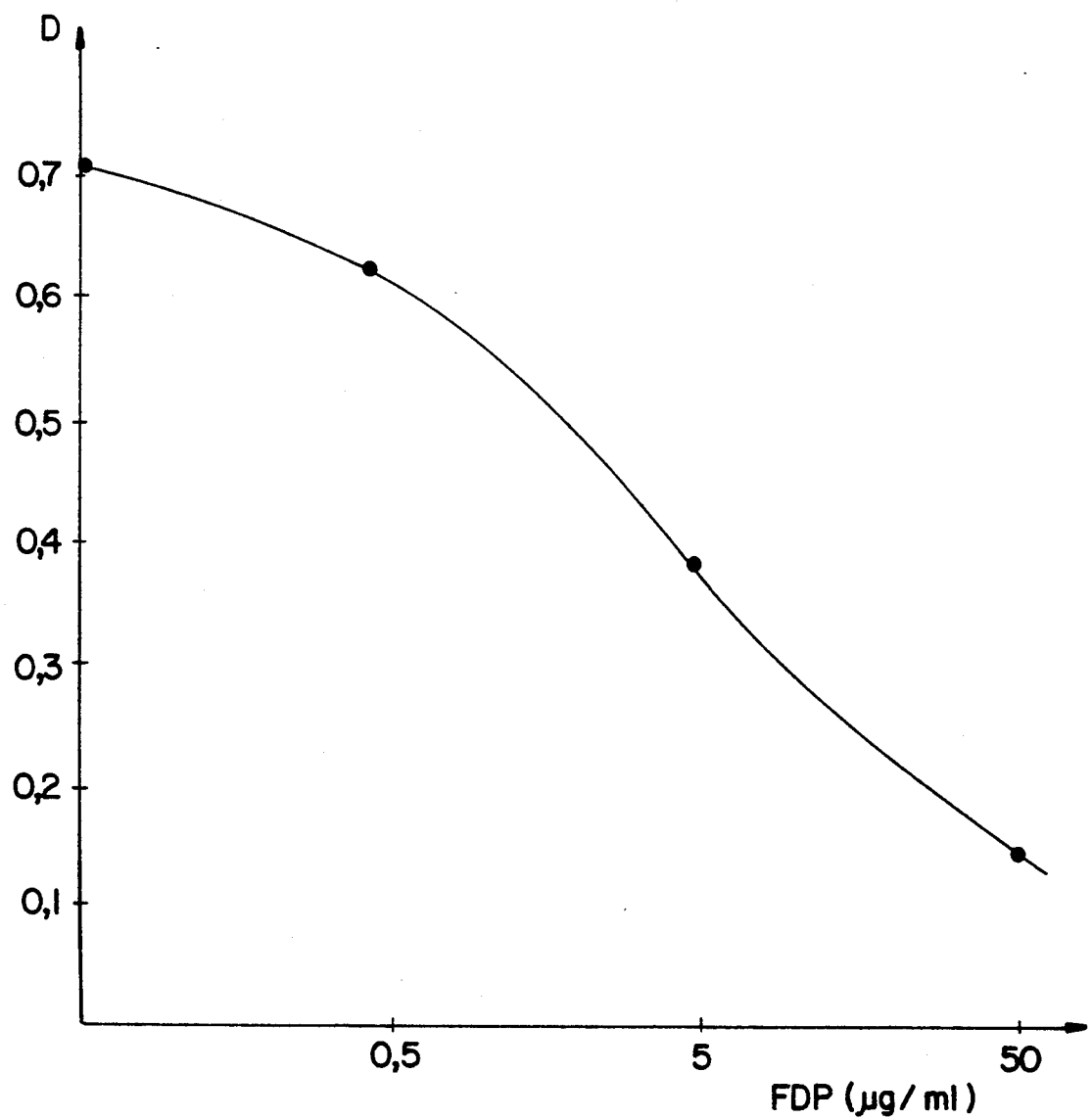

FIG. 8 below gives the agglutination inhibition curve for the latex/FDP reagent in the system optical density D (on the ordinate)/FDP concentration expressed in µg/ml (on the abscissa) at 600 nm.

According to the invention, assay kits are recommended which contain especially, suspended in an aqueous liquid, (i) latex microspheres intended to be bound to the user's immunological substance by adsorption, or (ii) immunological reagents in which the immunological substance is adsorbed on each of the microspheres so as to form especially an immunological reagent which is useful particularly in the field of hemostasis, such as latex/FDP, latex/anti-FDP, latex/anti-AT III or latex-/AT III.

COMPARATIVE EXPERIMENTS

Two series of comparative experiments were undertaken with immunological reagents prepared from the following carboxylated latices (having a proportion of 250–350 microequivalents of COOH or COOR′ groups) in the form of beads with a diameter of 55 to 70 nm (the respective proportions of the comonomers are expressed in molar percentages):

Latex A: polypropylene
Latex B: styrene/butyl methacrylate (52/48)
Latex C: methyl acrylate/butyl methacrylate (55/45)
Latex D: styrene/butadiene (55/45)
Latex E: styrene/butadiene/butyl methacrylate (50/25/25) to which anti-FDP antibodies were bound by covalency (series A) or adsorption (series B), in order to compare them with the immunological reagents obtained from said anti-FDP antibodies and latex 1 by covalency (Example 1) and adsorption (Example 5), respectively.

The stability during storage at 4° C. for at most 180 days at a concentration of 1% w/v was assessed. The results obtained are shown in Tables A and B below, which correspond to series (A) and (B) respectively.

TABLE A

STABILITY OF IMMUNOLOGICAL REAGENTS IN WHICH THE IMMUNOLOGICAL MATERIAL IS COVALENTLY BOUND

| Latex | Autoagglutination |
|---|---|
| Latex 1 | no agglutination at D = 180 |
| Latex A | autoagglutination at D = 110 |
| Latex B | autoagglutination at D = 150 |
| Latex C | autoagglutination at D = 142 |
| Latex D | autoagglutination at D = 108 |
| Latex E | autoagglutination at D = 137 |

TABLE B

STABILITY OF IMMUNOLOGICAL REAGENTS IN WHICH THE IMMUNOLOGICAL MATERIAL IS BOUND BY ADSORPTION

| Latex | Autoagglutination |
|---|---|
| Latex 1 | no agglutination at D = 180 |
| Latex A | autoagglutination at D = 115 |
| Latex B | autoagglutination at D = 145 |
| Latex C | autoagglutination at D = 138 |
| Latex D | autoagglutination at D = 116 |
| Latex E | autoagglutination at D = 128 |

The results in Tables A and B demonstrate the value of choosing the latex as regards the stability of the immunological reagent according to the invention, latex 1 not giving rise to any autoagglutination for a period of at least 180 days.

What is claimed is:

1. A method of binding an immunological material, selected from antigens and antibodies, to submicron latex particles by covalency or adsorption, in which method, which comprises the stabilization of the latex,
    (A) (1) acrylic latex particles based on polybutyl methacrylate, whose mean diameter is less than or equal to 100 nm, said latex containing a molar quantity of butyl methacrylate units greater than 50%, having a density of 0.9 to 1.4 g/cm$^3$ and containing from 100 to 450 microequivalents of COOH groups per gram of latex,
are brought into contact, in an appropriate liquid medium having an ionic strength in the range from 0.01 to 0.5 at a pH of 4 to 10, at a temperature of 0° to 60° C., with
    (2) the immunological material
to give latex particles sensitized by an immunological material and such that said immunological material is bound to each latex particle, and
    (B) said immunological reagent obtained in this way is stabilized by means of a stabilizing material selected from the group consisting of hydroxylated substances containing one or, several OH groups per molecule, protein-type substances, peptide-type substances, amino acids, polyose-type substances containing one or more carboxylic acid and/or carboxylate groups, polyvinylpyrrolidone and mixtures thereof.

2. A method according to claim 1, wherein said acrylic latex contains a molar quantity of butyl methacrylate units of 55 to 60%.

3. A method according to claim 1, wherein said acrylic latex is a copolymer essentially consisting of styrene units and butyl methacrylate units in a molar ratio styrene units/butyl methacrylate units of 40/60 to 45/55.

4. A method according to claim 1, wherein said acrylic latex is a copolymer essentially consisting of styrene units and butyl methacrylate units in a molar ratio styrene units/butyl methacrylate units of 42/58 to 43/57, and wherein said acrylic latex has a density of 1.0 to 1.1 g/cm$^3$ and contains from 250 to 300 microequivalents of COOH groups per gram of latex.

5. A method according to claim 1, wherein the contacting process of section (A) is carried out in a liquid medium comprising said stabilizing material of section (B).

6. A method according to claim 1, wherein the stabilization of section (B) is carried out after the contacting process of section (A).

7. A method according to claim 1, wherein said latex particles have a mean diameter of between 10 and 100 nm.

8. A method according to claim 1 for covalent binding of said immunological material to said latex particles, which comprises bringing said immunological material into contact, for at least 10 minutes, in an aqueous medium buffered to a pH of 4–10 and having an ionic strength of 0.01 to 0.5, with said latex particles in which the active COOH and COOR' sites have been sensitized beforehand by means of a carbodiimide compound, and then adding an excess of a stabilizing material to block the active sites which are still free on said latex particles.

9. A method according to claim 8, which comprises, prior to the contacting process, reacting the active sites of said latex particles with a difunctional chain-extending compound, in an aqueous medium buffered to pH 4–10 and having an ionic strength of 0.01 to 0.5, at a temperature of 40°–60° C., for at least 10 minutes.

10. A method according to claim 8, which comprises carrying out the contacting process with latex particles containing, on the surface, a molecular binding layer of a material selected from albumin and polylysine.

11. A method according to claim 1 for binding of said immunological material to said latex particles by adsorption, which comprises bringing said immunological material into contact with said latex particles for at least 1 h, in an aqueous medium buffered to a pH of 4–10 and having an ionic strength of 0.01 to 0.5, and then adding an excess of a stabilizing material to block the active sites which are still free on said latex particles.

12. A method according to any one of claims 1, 8 or 11, wherein said immunological material is brought into contact with said latex particles in a glycine buffer at pH 8.35.

13. A method according to claim 1, wherein 100 parts by weight of latex particles are brought into contact, in accordance with section (A), with 1 to 50 parts by weight of immunological material, and wherein 10 to 100 parts by weight of stabilizing material are used per 100 parts by weight of latex particles used in said contacting process.

14. An immunological reagent consisting of submicron latex particles to which an immunological material has been bound by covalency or adsorption, which reagent is obtained by the method of claim 1 and wherein said particles are (i) coated with said immunological material and said stabilising material and suspended in an aqueous liquid medium, and wherein said coated particles are invisible when exposed to radiation with a wavelength (λ) greater than the mean diameter (d) of said particles, and (ii) wherein said coated particles become "visible" due to agglutination when exposed to said radiation after having been brought into contact with a substance selected from the group consisting of antibodies and antigens which specifically bind said immunological material bound to said particles, the ratio λ/d being greater than or equal to 5/1.

15. A method according to claim 1, wherein said stabilized immunological reagent is brought into contact with a complementary or conjugate substance for said immunological material, in an aqueous liquid medium having a pH in the range from 4 to 10 and an ionic strength in the range from 0.01 to 0.5 and further wherein the change in agglutination is assessed by exposure to radiation with a wavelength (λ) in the range from 300 to 1000 nm and such that the ratio λ/d is greater than or equal to 5.

16. A method according to claim 8, wherein the active COOH and COOR' sites of the latex particles are sensitized beforehand with a carbodiimide compound and a glutaraldehyde compound, respectively.

17. A method according to claim 15, wherein said radiation is in the range from 400–700 nm.

18. A method according to claim 1, wherein 100 parts by weight of latex particles are brought into contact, in accordance with section (A), with 2 to 20 parts by weight of immunological material, and wherein 10 to 100 parts by weight of stabilizing material are used per 100 parts by weight of latex particles used in said contacting process.

* * * * *